US00PP35612P2

(12) United States Plant Patent
Sakazaki

(10) Patent No.: US PP35,612 P2
(45) Date of Patent: Jan. 30, 2024

(54) ***HYDRANGEA* PLANT NAMED 'WNHYDFBWMH'**

(50) Latin Name: ***Hydrangea* hybrid**
Varietal Denomination: WNHYDFBWMH

(71) Applicant: Wingen, LLC, Mustang Ridge, TX (US)

(72) Inventor: Ushio Sakazaki, Shiga (JP)

(73) Assignee: WinGen LLC, Mustang Ridge, TX (US)

( * ) Notice: Subject to any disclaimer, the term of this patent is extended or adjusted under 35 U.S.C. 154(b) by 0 days.

(21) Appl. No.: 18/118,404

(22) Filed: Mar. 7, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Cassandra Bright

(57) ABSTRACT

A new and distinct cultivar of *Hydrangea* plant named 'WNHYDFBWMH' is disclosed, characterized by mophead inflorescences, emerging from both terminal and lateral buds. Green sepals fade to white with green streaks. Plants flower early, and have mounded, cascading habits. The new variety is a *Hydrangea*, typically produced as an outdoor ornamental plant.

4 Drawing Sheets

Latin name of the genus and species: *Hydrangea* hybrid. Variety denomination: 'WNHYDFBWMH'.

BACKGROUND OF THE INVENTION

The new cultivar is a product of a planned breeding program conducted by the inventor, at a commercial nursery in Higashiomi, Shiga, Japan. The objective of the breeding program was to produce new mophead *Hydrangea* varieties with cascading habits. The crossing resulting in the new variety was made in May of 2016.

The seed parent is the variety *Hydrangea macrophylla*, 'Sugar White', unpatented. The pollen parent is an unnamed, unpatented specimen of the variety *Hydrangea luteovenosa*.

The new variety was found and selected by the inventor in June of 2018 at the same nursery in Higashiomi, Shiga, Japan.

Asexual reproduction of the new cultivar 'WNHYDFBWMH' was first performed during October of 2018 in Higashiomi, Shiga, Japan, by terminal cuttings. Through subsequent propagation, multiple additional generations have been reproduced, having shown that the unique features of this cultivar are stable and reproduced true to type.

SUMMARY OF THE INVENTION

The cultivar 'WNHYDFBWMH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WNHYDFBWMH.' These characteristics in combination distinguish 'WNHYDFBWMH' as a new and distinct *Hydrangea* cultivar:

1. Mophead inflorescences which emerge from both terminal and lateral buds.
2. Sepals emerge lime green and fade to white but maintain occasional streaks or mottling of green along sepal length.
3. Cascading/trailing type habit.
4. Leaf shape and size is more narrowly elliptic than *Hydrangea macrophylla* but larger than *Hydrangea luteovenosa*.

PARENT COMPARISONS

Plants of 'WNHYDFBWMH' are similar to plants of the seed parent in most horticultural characteristics, however, plants of 'WNHYDFBWMH' differ in the following:

1. Flowers of the new variety occur on terminal and lateral buds, while flowers of the seed parent set only on terminal buds.
2. The new variety flowers earlier than the seed parent.
3. Growth habit of the new variety is weeping/cascading, while the growth habit of the seed parent is upright.

Plants of 'WNHYDFBWMH' are similar to plants of the pollen parent in most horticultural characteristics, however, plants of 'WNHYDFBWMH' differ in the following:

1. Flower sepals of the new variety are larger than flower sepals of the pollen parent.
2. Inflorescences of the new variety are mophead, while inflorescences of the pollen parent are lacecap.

COMMERCIAL COMPARISON

Plants of the new cultivar *Hydrangea* 'WNHYDFBWMH' can be compared to the commercial variety *Hydrangea* 'USHYD0405', U.S. Plant Pat. No. PP31,120. Plants of 'WNHYDFBWMH' are similar to plants of 'USHYD0405' in most horticultural characteristics, however, plants of 'WNHYDFBWMH' differ in the following:

1. Inflorescences of the new variety are mophead, while inflorescences of this comparator are lacecap.
2. Flowers of the new variety open lime green, fading to white with some remaining green streaks. Flowers of this comparator open and remain white.

BRIEF DESCRIPTION OF THE PHOTOGRAPHS

The accompanying photograph in FIG. 1 illustrates in full color a typical plant of 'WNHYDFBWMH' grown in a poly-greenhouse in Grand Haven, Michigan. This plant is approximately 2-3 years old, grown in a 2-gallon container.

Figure 1:
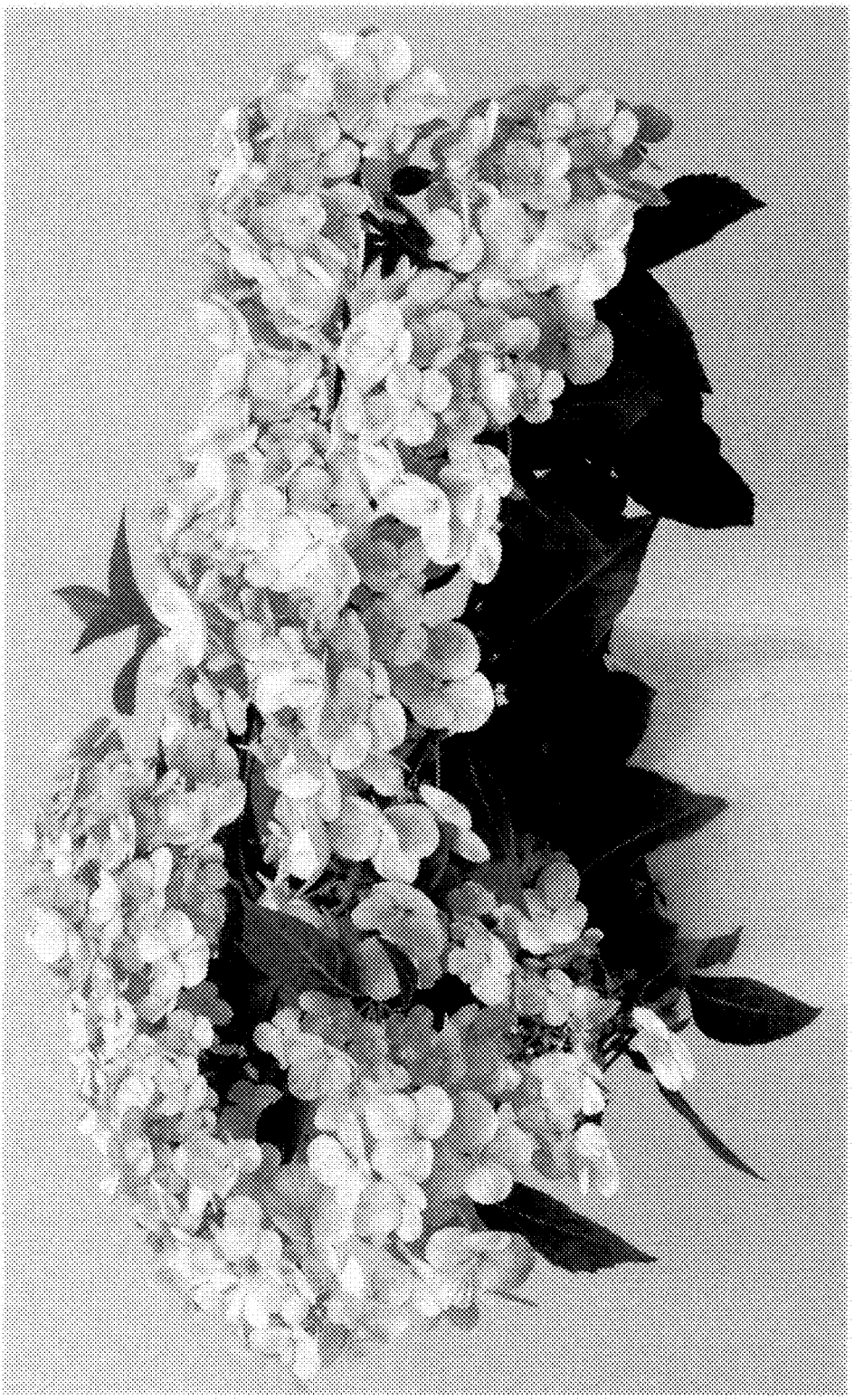
Figure 2:
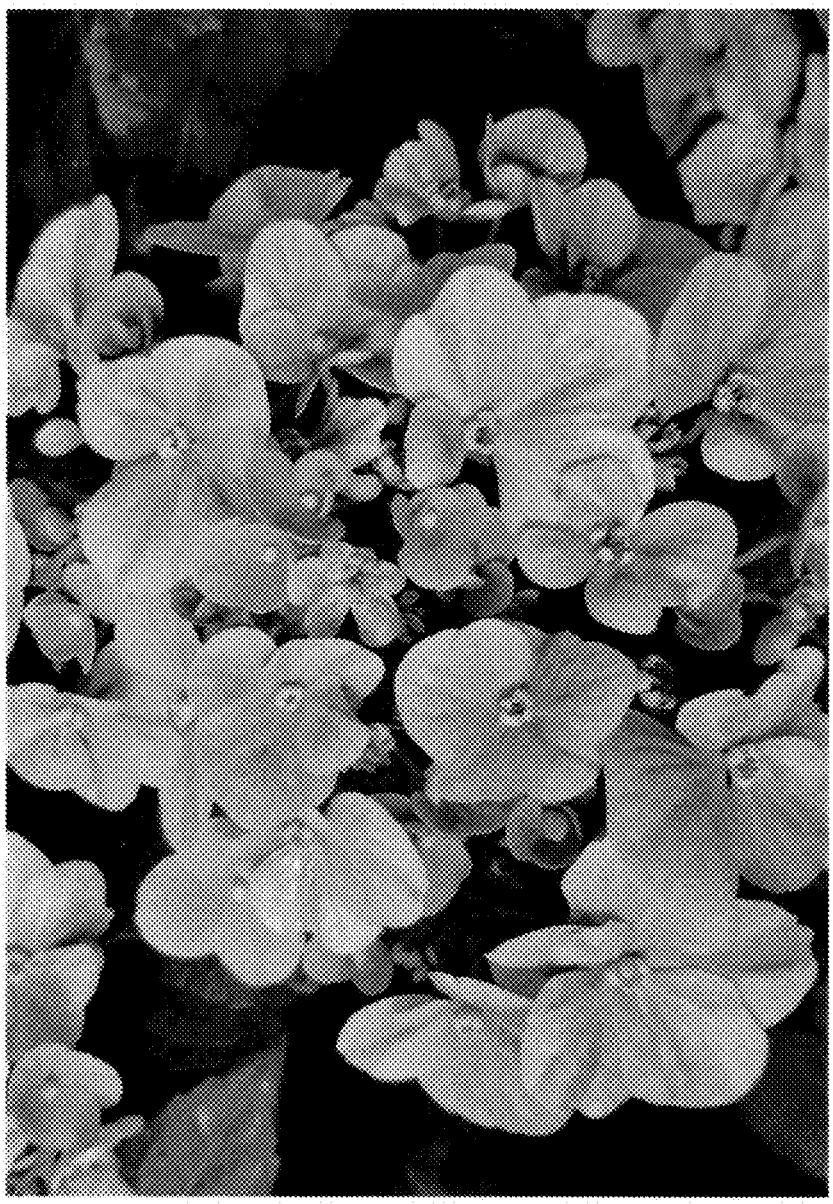
FIG. 2 illustrates in full color a close up of an immature inflorescence of 'WNHYDFBWMH'.
Figure 3:
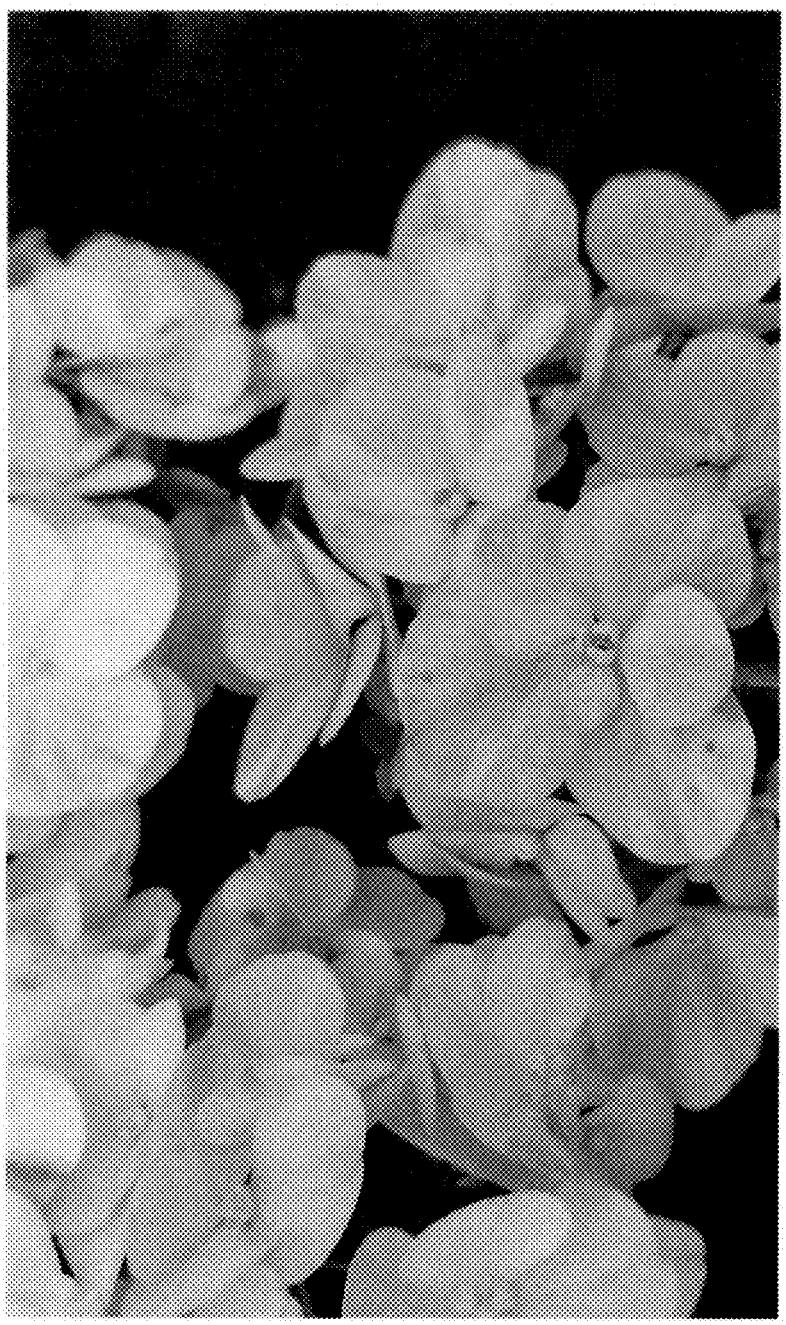
FIG. 3 illustrates in full color a close up of a mature inflorescence of 'WNHYDFBWMH, still having significant green coloration.
Figure 4:
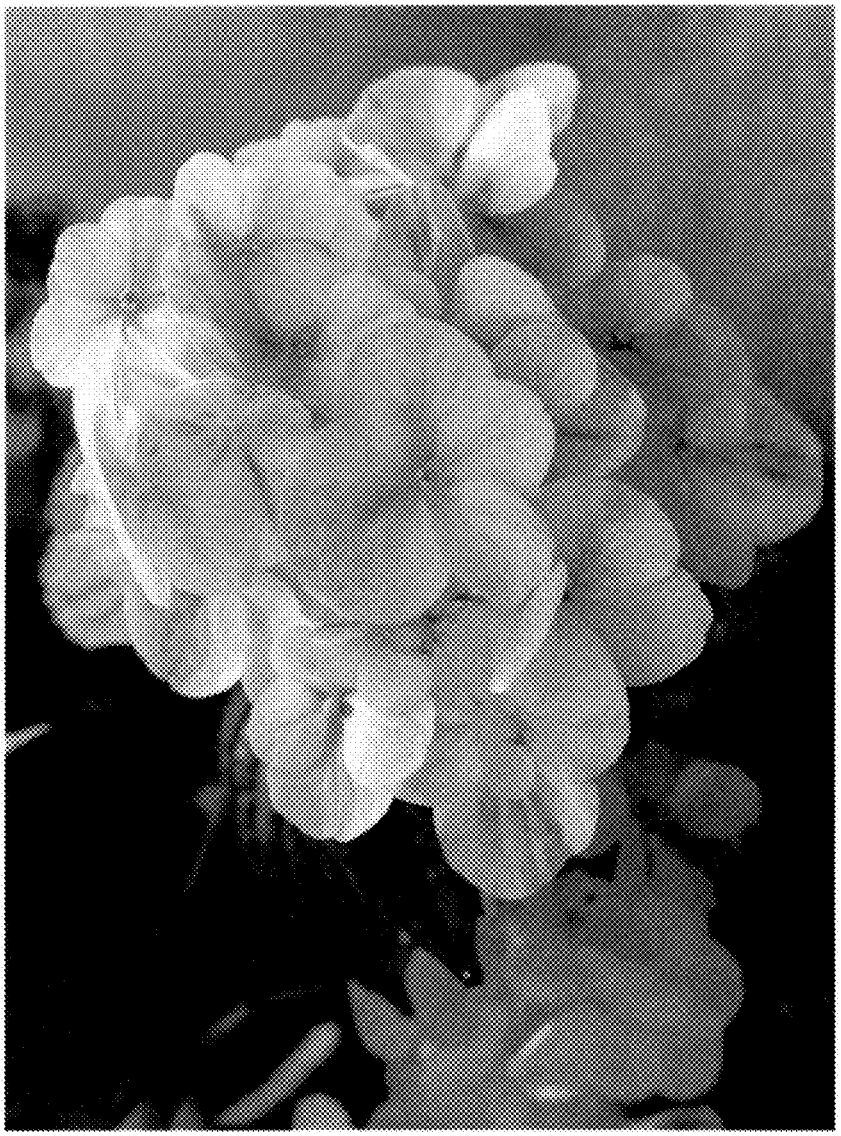
FIG. 4 illustrates in full color a close up of a mature inflorescence, more mature than that of FIG. 3 of 'WNHYDFBWMH, having residual streaks of green.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'WNHYDFBWMH' plants grown outdoors in Grand Haven, Michigan. The plants were about 2 to 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Hydrangea* hybrid 'WNHYDFBWMH'.

PROPAGATION

Typical method: Terminal cuttings.
Root initiation: 5 to 7 days in the summer.
Time to produce rooted cutting: 28 days in the summer.
Roots: Thin to medium, freely branching, fibrous, moderately dense. Beige to tan in color, not accurately measured with RHS chart.

PLANT

Growth habit: Upwards and outwards in a drooping manner.
Shape: Trailing.
Height: 25 cm.
Plant spread: 55 cm.
Pot size of plant described: #3 container.
Age of plant described: Approximately 2 to 3 years.
Growth rate: Good.
Plant vigor: Quite vigorous.
Stem:
- *Branching.*—Basal.
- *Number of lateral branches.*—20 to 30.
- *Shape.*—Rounded.
- *Color.*—Immature: RHS Yellow-Green 145A. Mature: RHS Yellow-Green 145A.
- *Length.*—30 cm.
- *Width.*—4 mm.
- *Aspect.*—0 to 45°.
- *Strength.*—Good.
- *Pubescence.*—None.
- *Internode length.*—4 cm.

FOLIAGE

Leaf:
- *Arrangement.*—Opposite.
- *Shape.*—Narrowly elliptic.
- *Length.*—9 cm.
- *Width.*—3.5 cm.
- *Apex.*—Acuminate.
- *Base.*—Cuneate.
- *Margin.*—Serrulate.
- *Texture of top surface.*—Smooth, glabrous.
- *Texture of bottom surface.*—Glabrous with pronounced venation.
- *Pubescence.*—None.
- *Color.*—Young Foliage Upper Side: RHS Yellow-Green 144A. Young Foliage Under Side: Near RHS Yellow-Green 146D. Mature Foliage Upper Side: RHS Yellow-Green 147A. Mature Foliage, Under Side: RHS Yellow-Green 147B.

Venation:
- *Type.*—Pinnate.
- *Color.*—Mature, Upper Side: RHS Yellow-Green 145A. Mature, Under Side: RHS Yellow-Green 145A.

Petiole:
- *Length.*—5 mm.
- *Width.*—2 mm.
- *Color.*—Upper Side: RHS Yellow-Green 145A, with Greyed-Orange 173D tint. Under Side: RHS Yellow-Green 145A, with Greyed-Orange 173D tint.
- *Texture.*—Upper Side: Glabrous. Under Side: Glabrous.

INFLORESCENCE

Natural flowering season: May to July.
Inflorescence type: Mophead.
Panicle:
- *Shape.*—Globular, with a flat base; umbel.
- *Height.*—12 cm.
- *Diameter.*—15 cm.

Fragrance: None.
Sterile flowers:
- *Flowers per inflorescence.*—50 to 75.
- *Aspect.*—Upright and outward.
- *Shape.*—Single whorl.
- *Length.*—5 cm.
- *Diameter.*—5 cm.
- *Depth.*—1 mm.
- *Persistence.*—Persistent.

Bud:
- *Length.*—3 mm.
- *Diameter.*—2 mm.
- *Shape.*—Obovate.
- *Color.*—RHS Yellow-Green 144D.

Petals:
- *Number per flower.*—4.
- *Arrangement.*—Cruciform.
- *Shape.*—Elliptic.
- *Tip.*—Acute.
- *Base.*—Flattened.

*Margin.*—Entire.
*Length.*—3 mm.
*Width.*—2 mm.
*Texture.*—Upper side: Glabrous. Under side: Glabrous.
*Color.*—When Opening, Upper Side: RHS Yellow-Green 144B-C. When Opening, Under Side: RHS Yellow-Green 144B-C. Fully Opened, Upper Side: RHS White NN155B. Fully Opened, Under Side: RHS White NN155B.

Sepal:
*Number.*—4 to 5.
*Arrangement.*—Single whorl.
*Shape.*—Elliptic to globose.
*Tip.*—Obtuse, sometimes slightly retuse.
*Base.*—Slightly attenuate.
*Margin.*—Entire.
*Length.*—2.5 cm.
*Width.*—2.25 cm.
*Texture.*—Upper side: Soft and silky. Under side: Soft and silky.
*Color.*—When Opening, Upper Side: RHS Yellow-Green 144B and 144C. When Opening, Under Side: RHS Yellow-Green 144B and 144C. Fully Opened, Upper Side: RHS Yellow-Green 144B and 144C. Fully Opened, Under Side: RHS Yellow-Green 144B and 144C. Fading, Upper Side: RHS White NN155B with occasional streaks or mottling of Yellow-Green 144C along sepal length. Fading, Under Side: RHS White NN155B with occasional streaks or mottling of Yellow-Green 144C along sepal length.

Pedicel:
*Length.*—2 cm.
*Diameter.*—2 mm.
*Angle.*—45° relative to stem.
*Strength.*—Good, somewhat flexible.
*Texture.*—Slightly pubescent.
*Color.*—RHS White NN155B with Greyed-Red 181C developing near base (about last 2mm).

Fertile flowers:
*Flowers per inflorescence.*—About 50.
*Aspect.*—Upright.
*Shape.*—Round, single whorl of petals with irregularly shaped sepals.
*Length.*—1.5 cm.
*Diameter.*—1 cm.
*Depth.*—0.5 cm.
*Persistence.*—Self-cleaning.

Bud:
*Length.*—4 mm.
*Bud diameter.*—3 mm.
*Bud shape.*—Obovate.
*Bud color.*—RHS Yellow-Green 144D.

Petals:
*Number per flower.*—5.
*Arrangement.*—Stellate.
*Shape.*—Elliptic.
*Tip.*—Acute.
*Base.*—Flattened.
*Margin.*—Entire.
*Length.*—4 mm.
*Width.*—3 mm.
*Texture.*—Upper Side: Soft and silky. Under Side: Soft and silky.
*Color.*—When Opening, Upper Side: RHS Yellow-Green 144B-C. When Opening, Under Side: RHS Yellow-Green 144B-C. Fully Opened, Upper Side: RHS White NN155B. Fully Opened, Under Side: RHS White NN155B.

Sepal:
*Number.*—4.
*Arrangement.*—Cruciform.
*Shape.*—Expanded and irregularly shaped, crescent shaped.
*Tip.*—Obtuse.
*Base.*—Attenuate.
*Margin.*—Entire.
*Length.*—Unexpanded.—3 mm. Expanded.—1 to 2 cm.
*Width.*—2.25 cm.
*Texture.*—Upper Side: Smooth and silky. Under Side: Smooth and silky.
*Color.*—When Opening, Upper Side: RHS Yellow-Green 144B and 144C. When Opening, Under Side: RHS Yellow-Green 144B and 144C. Fully Opened, Upper Side: RHS Yellow-Green 144B and 144C. Fully Opened, Under Side: RHS Yellow-Green 144B and 144C. Fading, Upper Side: RHS White NN155B with occasional streaks or mottling of Yellow-Green 144C along sepal length. Fading, Under Side: RHS White NN155B with occasional streaks or mottling of Yellow-Green 144C along sepal length.

Pedicel:
*Length.*—5 mm.
*Diameter.*—1 mm.
*Angle.*—90° relative to stem.
*Strength.*—Good, somewhat flexible.
*Texture.*—Slightly pubescent.
*Color.*—White 155D flushed Yellow-Green 144C.

REPRODUCTIVE ORGANS

Sterile flower:
Pistil:
*Number.*—1.
*Length.*—3 mm.
Stigma:
*Shape.*—2-lobed, fused.
*Color.*—RHS Yellow-Green 145B.
*Style length.*—Less than 1 mm.
*Style color.*—RHS Yellow-Green 145B.

Fertile flower:
Stamens:
*Number.*—10.
*Filament length.*—5 mm.
*Filament color.*—RHS White NN155B.
Anthers:
*Shape.*—Oblong.
*Length.*—1 mm.
*Color.*—RHS Yellow-Green 145B.
*Pollen Amount.*—Sparse.
Pistil:
*Number.*—1.
*Length.*—3 mm.
Stigma:
*Shape.*—3-lobed, fused.
*Color.*—RHS Yellow-Green 145B.
*Style length.*—Less than 1 mm.
*Style color.*—RHS Yellow-Green 145B.

OTHER CHARACTERISTICS

Disease resistance: Neither resistance nor susceptibility to the normal diseases and pests of *Hydrangea* has been observed.

Drought tolerance and cold tolerance: The new cultivar can tolerate cold temperatures to approximately −31° C. and tolerates an upper temperature range to at least 38° C.

Fruit/seed production: Not observed to date.

What is claimed is:

1. A new and distinct cultivar of *Hydrangea* plant named 'WNHYDFBWMH' as herein illustrated and described.

* * * * *